US012709715B2

(12) United States Patent
Despres et al.

(10) Patent No.: US 12,709,715 B2
(45) Date of Patent: Aug. 18, 2026

(54) METHOD FOR PRODUCING A BIOFUEL BY STEAM CRACKING

(71) Applicant: EUROPEENNE DE BIOMASSE, Paris (FR)

(72) Inventors: Jean-Luc Despres, Verzenay (FR); Thomas Habas, Paris (FR); Adriana Quintero-Marquez, Le Vesinet (FR); Frédéric Martel, Riems (FR)

(73) Assignee: EUROPEENNE DE BIOMASSE, Paris (FR)

( * ) Notice: Subject to any disclaimer, the term of this patent is extended or adjusted under 35 U.S.C. 154(b) by 24 days.

(21) Appl. No.: 17/597,054

(22) PCT Filed: Jun. 17, 2020

(86) PCT No.: PCT/FR2020/051043
§ 371 (c)(1),
(2) Date: Dec. 23, 2021

(87) PCT Pub. No.: WO2020/260798
PCT Pub. Date: Dec. 30, 2020

(65) Prior Publication Data

US 2022/0315853 A1 Oct. 6, 2022

(30) Foreign Application Priority Data

Jun. 24, 2019 (FR) ....................................... 1906794

(51) Int. Cl.
*C10L 5/44* (2006.01)
*B09B 3/32* (2022.01)
(Continued)

(52) U.S. Cl.
CPC .................. *C10L 9/08* (2013.01); *B09B 3/32* (2022.01); *C10L 5/44* (2013.01); *G16C 20/10* (2019.02);
(Continued)

(58) Field of Classification Search
CPC ............... C10L 5/44; C10L 2200/0469; C10L 2290/58; C10L 2290/60; C10L 2290/148
See application file for complete search history.

(56) References Cited

U.S. PATENT DOCUMENTS 5,266,270 A * 11/1993 Ajot ....................... G01N 31/00 422/89
7,501,285 B1 * 3/2009 Triche .................... G01N 21/64 436/139
(Continued)

FOREIGN PATENT DOCUMENTS

CN 105806735 A 7/2016
EP 2373767 B1 7/2018
(Continued)

OTHER PUBLICATIONS

Ademe Final Report, (Sep. 2017), Referentiels Combustibles Bois Energie de l'Ademe, 78 pages.
(Continued)

*Primary Examiner* — Ellen M Mcavoy
*Assistant Examiner* — Ming Cheung Po
(74) *Attorney, Agent, or Firm* — TraskBritt

(57) ABSTRACT

A method for producing a biofuel by continuous or discontinuous steam cracking of lignocellulosic biomass includes: —recording a digital model of the optimal steam cracking parameters as a function of the nature and the content of the contaminants; —introducing a biomass containing at least part of the contaminated biomass into the steam cracking reactor; —measuring at least once during the treatment the nature and content of the contaminants; and—controlling the adjustment of the steam cracking parameters as a function of the nature and the content of the measured contaminants and of the digital model.

9 Claims, 1 Drawing Sheet

(51) Int. Cl.

| | |
|---|---|
| ***C10L 9/08*** | (2006.01) |
| ***G16C 20/10*** | (2019.01) |
| ***G16C 60/00*** | (2019.01) |
| *B09B 3/45* | (2022.01) |
| *B09B 101/85* | (2022.01) |

(52) U.S. Cl.

CPC ................ *G16C 60/00* (2019.02); *B09B 3/45* (2022.01); *B09B 2101/85* (2022.01); *C10L 2200/0469* (2013.01); *C10L 2290/148* (2013.01); *C10L 2290/58* (2013.01); *C10L 2290/60* (2013.01)

(56) References Cited

U.S. PATENT DOCUMENTS

| | | | | |
|---|---|---|---|---|
| 9,534,840 | B2 * | 1/2017 | Pahwa | F26B 5/16 |
| 2013/0211733 | A1 * | 8/2013 | Baeveghems | C07C 1/20 702/24 |
| 2013/0341569 | A1 * | 12/2013 | Ampulski | C10L 9/083 422/162 |
| 2013/0341596 | A1 | 12/2013 | Chang et al. | |
| 2014/0083939 | A1 * | 3/2014 | Nguyen | C12M 45/03 210/612 |
| 2019/0359905 | A1 * | 11/2019 | Lanni | C10L 10/12 |

FOREIGN PATENT DOCUMENTS

| | | | | |
|---|---|---|---|---|
| JP | 2012-229326 A | | 11/2012 | |
| JP | 2018-059051 A | | 4/2018 | |
| WO | 2010/071440 A1 | | 6/2010 | |
| WO | WO-2012109490 A2 | * | 8/2012 | F23G 5/02 |
| WO | WO-2020260798 A1 | * | 12/2020 | G16C 60/00 |

OTHER PUBLICATIONS

B. V. Babu. “Biomass pyrolysis: a state-of-the-art review” Biofuels, Bioproducts & Biorefining, GB, vol. 2, No. 5, Sep. 1, 2008 (Sep. 1, 2008), pp. 393-414.

International Search Report for International Application No. PCT/FR2020/051043, mailed Dec. 9, 2021, 10 pages (4 pages of English Translation and 6 pages of Original Document).

International Written Opinion for International Application No. PCT/FR2020/051043, mailed Dec. 9, 2021 17 pages (8 pages of English Translation and 9 pages of Original Document).

Ramos Ana et al. “Co-gasification and recent developments on waste-to-energy conversion: A review” Renewable and Sustainable Energy Reviews, vol. 81, Aug. 7, 2017 (Aug. 7, 2017), pp. 380-398.

Sagehashi M et al. “Superheated steam pyrolysis of biomass elemental components and Sugi (Japanese cedar) for fuels and chemicals” Bioresource Technology, Elsevier, Amsterdam, NL, vol. 97, No. 11, Jul. 1, 2006 (Jul. 1, 2006), pp. 1272-1283.

Chinese Office Action for Application No. 202080058052.8 dated Oct. 31, 2023, 10 pages.

Indian Office Action for Application No. 202217003035 dated Nov. 3, 2023, 6 pages.

Japanese Office Action for Application No. 2021-576620 dated Jan. 9, 2024, 8 pages.

Chinese Search Report for Chinese Application No. 202080058052, dated Oct. 31, 2023, 1 pages.

European Communication pursuant to Article 94(3) EPC for European Application No. 20742354.2, dated Oct. 8, 2024, 5 pages.

Japanese Decision of Refusal for Japanese Application No. 2021-576620, dated May 14, 2024, 15 pages with English translation.

Notification to Grant Patent Right for Invention for Chinese Application No. 202080058052, dated Jul. 2, 2024, 3 pages with English translation.

Canadian Office Action for Application No. 3,144,993 dated Apr. 17, 2025, 12 pages with machine translation.

Stelte, Wolfgang, Steam Explosion for Biomass Pre-Treatment, Danish Technological Institute (2013, pp. 1-15.

Stinson, Mary K., Foster Wheeler Enviresponse, Inc., Contaminants and Remedial Options at Wood Preserving Sites, Risk Reduction Engineering Laboratory Office of Research and Development U.S. Environmental Protection Agency, (Oct. 1992), 144 pages.

* cited by examiner

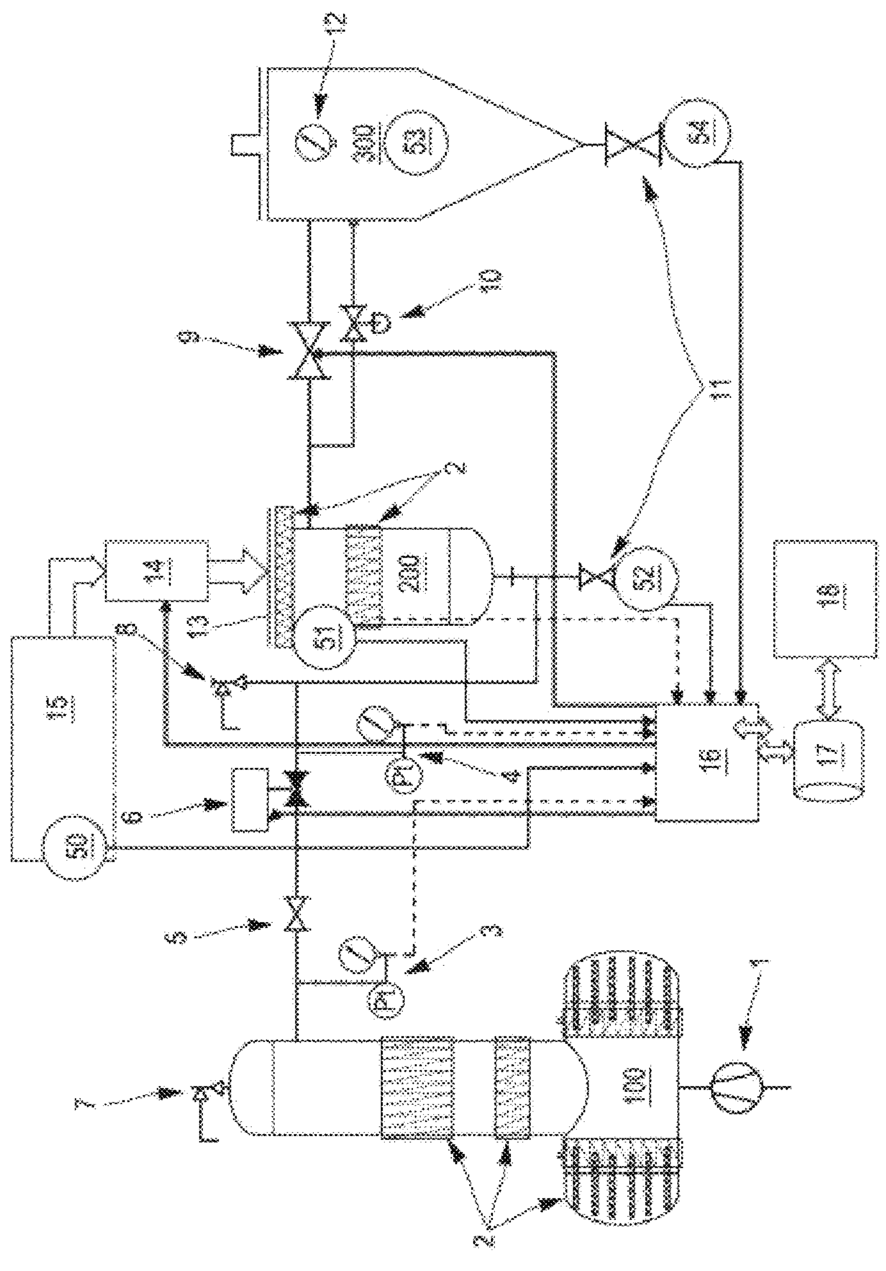
12
300
53
54
10
9
11
2
14
200
13
51
52
18
8
15
16
17
4
P1
6
50
5
3
P1
7
100
1
2

METHOD FOR PRODUCING A BIOFUEL BY STEAM CRACKING

CROSS-REFERENCE TO RELATED APPLICATIONS

This application is a national phase entry under 35 U.S.C. § 371 of International Patent Application PCT/FR2020/051043, filed Jun. 17, 2020, designating the United States of America and published as International Patent Publication WO 2020/260798 A1 on Dec. 30, 2020, which claims the benefit under Article 8 of the Patent Cooperation Treaty to French Patent Application Serial No. 1906794, filed Jun. 24, 2019.

TECHNICAL FIELD

The present disclosure relates to the production of solid biofuels originating from treatment of biomass of various origins, by way of a steam cracking or steam explosion method.

BACKGROUND

Biomass is a renewable primary energy that can be transported to its transformation site, but is a low-density, variable and perishable source of energy.

The transformation of lignocellulosic biomass (wood, agricultural waste, co-products of agriculture and the agro-industry) into an energy-dense, transportable, and easily storable compound, makes it possible to develop and consolidate a stationary energy industrial sector (biofuel used at a fixed point, at home, in contrast with biofuel oils), and to reduce the environmental impacts ($CO_2$ fossil emission, with a biomass without fertilizers or phytosanitaries).

The heat treatment of the biomass by steam cracking allows for this densification of energy, and modifies the structure of the treated biomass:

- the lignocellulosic materials are defibrillated;
- the crystallinity of the cellulose is increased as a result of the crystallization of the amorphous portions;
- the hemicelluloses are easily hydrolyzed; and
- the delignification is promoted as a result of modifications in the structure of the lignin.

The steam explosion is a biomass treatment that is commonly used for the production of biofuels, in particular, in the form of granules ("black pellets"). It simultaneously uses both physical/mechanical methods and chemical methods in order to break the structure of the lignocellulosic material. In general terms, steam explosion is a violent evaporation or flash evaporation of water into steam. The pressurized containers that operate above atmospheric pressure can also provide the conditions for rapid boiling, which can be characterized as steam explosion. The biomass introduced into a steam cracking reactor, continuously or in batches, is rapidly heated by way of saturated steam under high pressure. The biomass/steam mixture is retained for a period of time, in order to promote the hydrolysis of the hemicelluloses, and other chemical and physical changes. This period is then followed by explosive decompression. The steam explosion is typically initiated at a temperature of 160-260° C. for a few seconds to a few minutes, before the material is exposed to atmospheric pressure.

The apparatus for steam explosion consists in an evaporator (steam generator) and a reactor that is subjected to rapid decompression. Steam explosion can be described as being made up of two successive phases: steam cracking (i.e., breaking complex molecules into smaller molecules under the effect of steam), and explosive decompression.

The first phase consists in causing steam, under high pressure, to penetrate into the interior of the structure of the material. Thus, the steam condenses and wets the surface of the material. The condensed water initiates the hydrolysis of acetyl and methylglucuronic acid groups present in the hemicelluloses. The acids thus freed reduce the pH of the medium and catalyze the depolymerization of the hemicelluloses. The application of more drastic conditions allows for the formation of monosaccharides, while increasing the furfural and 5-hydroxymethylfurfural concentration, which are fermentation inhibitors.

During the second phase, the explosive decompression results in the instantaneous evaporation of some of the condensation water present in the structure. This expansion of the water vapor exerts a shearing force on the surrounding structure. If the shearing force is sufficiently high, the steam will cause the mechanical breakage of the lignocellulosic structures. The combined effects of the two stages include the modification of the physical properties of the material (specific surface area, water retention, coloration, crystallinity of the cellulose, etc.), the hydrolysis of the hemicellulosic compounds, and the modification of the chemical structure of the lignin, allowing for the opening of the material, and facilitating the extraction thereof.

The two parameters controlling the steam explosion are the reaction temperature and the residence time. The time that the biomass spends in the reactor helps to determine the degree of hydrolysis of the hemicelluloses by the organic acids. However, long residence times will also increase the production of degradation products, which must be minimized in a following fermentation method. The temperature controls the steam pressure in the reactor. Higher temperatures result in higher pressures, thus increasing the difference between the reactor pressure and the atmospheric pressure. The pressure difference is in turn proportional to the shearing force.

The parameters of the method are critical, and, in order to facilitate the comparison of different options, a model has been developed that is based on the hypotheses that the kinetics of the method is of the first order and obeys the Arrhenius law, making it possible to develop the ordinate of the reaction (R0):

$$R0 = \int \exp\left[(Tr - Tb)/14.75\right] dt$$

Where Tr is the reaction temperature (° C.), Tb is the baseline temperature (boiling point of water at atmospheric pressure (100° C.)), t is the residence time (min), and 14.75 is the conventional activation energy supposing that the general method is hydrolytic and that the general conversion is of the first order. The log 10 value of the ordinate of the reaction gives the severity factor (or severity) that is used to represent the effects of the steam explosion on the biomass:

$$\text{Severity} = \log 10(R0)$$

Generally, the production of biofuels by steam cracking is carried out starting from natural biomass, originating from logging or coppicing, or products derived from timber exploitation, or indeed other agricultural products, and the operating point is optimized so as to obtain a good energy quality for the steam-cracked powder.

However, today, the multiplication of biomass exploitation projects creates significant strain on the supply channels, in particular, of wood. The current uses tending toward pulpwood (particle panels and papermaking), or indeed on solid construction or furniture wood, push the price upward.

Furthermore, environmental politics aim to increase the recycling of products at the end of life, and to limit or indeed forbid solutions involving landfill of waste from industry. Most of the organic coproducts originating from biomass end up in an energy recovery unit, i.e., an incinerator.

The professionals of the wood industry use a usage classification that distinguishes the woods referred to as "A," the woods referred to as "B," and the woods referred to as "C," proposed by ADEME in the 2017 report "Référentiels combustibles bois énergie de l'ADEME" ["*ADEME fuel references wood energy"*].

The wood referred to as "A" is made up of non-coated and non-treated wooden packaging waste.

The wood referred to as "B" is made up of non-dangerous wood waste containing a low quantity of additives or other materials; glued wood, wood that has undergone a surface treatment (preservation, finishing), or that has received a coating (wallpaper, melamine, polypropylene). For this reason, this category includes panels, furniture wood, demolition wood free of rubble.

The wood referred to as "C" is, in turn, made up of dangerous waste (creosoted woods, for example), which is destroyed in a special waste incineration plant or used in cement kilns.

The steam-cracking differs from hydrothermal pre-treatment, also referred to as aqueous fractionation, solvolysis, hydrothermolysis, or hydrothermal treatment, in that the latter consists in using water at a high temperature and high pressure in order to promote the disintegration and the separation of the lignocellulosic matrix. This technique is not suitable for the production of black pellets, since the products obtained are largely liquid.

The pyrolysis is a chemical decomposition of an organic compound, by intense heating in the absence of oxygen. The compounds obtained following pyrolysis differ, in terms of their characteristics, from those obtained by steam cracking. The steam cracking cannot be likened to a pyrolysis technique, in that it uses steam explosion and is carried out in the presence of oxygen.

Pyrolysis techniques using digital models in order to optimize the parameters of their methods are known from, for example, the document WO2012/109490 or the document CN105806735A. These known pyrolysis techniques are based on the chemical decomposition of an organic compound, by intense heating in the absence of oxygen.

The document BV BABU "Biomass pyrolysis: a state of the art review" also describes a pyrolysis prior art.

U.S. Patent Application Publication No. US2013/341569 describes methods for pre-treatment of the biomass, comprising a step of steam cracking in order to generate the synthesis gas. The method also comprises a catalytic converter that uses a control system that, depending on the composition of the catalyst material, adjusts the gas conversion.

Finally, "Superheated steam pyrolysis of biomass elemental components and Sugi (Japanese cedar) for fuels and chemicals" relates to a method for pyrolysis, by way of superheated steam, of components of biomass, as well as Sugi (Japanese cedar), in order to produce fuels and chemical products. This document discloses a method using a digital model for superheated steam pyrolysis, the application of which is limited to specimens of some individual constituents of the biomass (xylan, cellulose, lignin, etc.), or to a single type of biomass, i.e., the Japanese cedar referred to as "native biomass" (Table 1 page 1273; right-hand column, page 1273, lines 1-5).

The European patent EP2373767B1 describes another example of a method for the production of pellets or compacts from a material containing lignin, in the form of treatable particles, comprising the steps of:

(a) passing the lignin-containing material, having a relative humidity content of from 0 to 20 wt. %, into a reactor;
(b) heating the lignin-containing material to 180 to 235° C. by injecting steam into the reactor;
(c) keeping the material in the reactor at the temperature reached between 1 to 12 minutes, in order to soften the material and release lignin;
(d) reducing the pressure in the reactor in at least one step; and
(e) shaping the treated material in order to form tablets or compacts.

The solutions of the prior art are not entirely satisfactory, since they make use of pyrolysis methods that do not make it possible to produce black pellets; either they provide for parameter control merely for a catalytic converter, or they require a supply of natural biomass, which can prove to be restrictive.

In the prior art, the use of a digital model is applied only:

to pyrolysis systems that do not make it possible to obtain compounds having the characteristics required for obtaining black pellets; and to systems that do not involve steam cracking parameterization in the digital model.

Indeed, the solutions of the prior art are designed to optimize the operating point, and, in particular, the severity factor, depending on the quality of the final product, i.e., the pulverulent material used for subsequently manufacturing the pellets, as well as the energy efficiency of the pellet production.

The particle size and the energy efficiency decrease when the severity factor increases.

Vice versa, if the severity factor is insufficient, the calorific value of the steam-cracked material reduces, and the product is more fibrous than pulverulent, which makes it difficult to shape it into pellets.

In the prior art, the use of contaminated biomass is excluded, in order to prevent the pollution of the pellets by residual contaminants.

It is certainly possible to clean the wood by soaking in various chemical, mineral, or organic solutions, requiring dilution, a loss of molecules by absorption by the wood, and causing an increase in the humidity. Other methods advocate high-temperature treatments, where the output product is a fuel gas, but the use of the gas is limited by the volatile contaminants. The technologies are expensive and immature, in a field where the value of the final product must be compatible with those of energy commodities.

The methods for decontaminating the products are meaningful only for cheaper reuse. In the case of furniture, it is more a case of repairing the object, or disassembling and recycling certain parts—for example, particle panels to panel-makers.

BRIEF SUMMARY

In order to overcome the disadvantages of the prior art regarding the lesser availability of natural biomass and the inadequacy of known facilities for the treatment of contaminated biomass, the present disclosure relates, according to the most general meaning thereof, to a method for producing a biofuel by steam cracking of biomass, wherein:

- a digital model of the optimal steam cracking parameters depending on the nature and the content of the contaminants is recorded;
- a biomass containing the contaminated biomass, at least in part, is introduced into the steam cracking reactor;
- the nature and content of the contaminants is measured at least once during the treatment; and
- the adjustment of the steam cracking parameters is controlled depending on the nature and the content of the measured contaminants and on the digital model.

Within the meaning of the present patent, "contaminated lignocellulosic biomass" means lignocellulosic biomass containing at least one substance that is not found naturally in natural biomass prior to treatment by human intervention. The contaminants are, for example, paints, varnishes, chemical additives, as well as metals or polymers, but also dead or living exogenic biological substances.

According to an advantageous embodiment, the contaminated lignocellulosic biomass has a humidity of less than 27% and directly undergoes a steam cracking treatment without any other preceding heat or chemical treatment.

Within the meaning of the present patent, "contaminating substances" or "contaminants" means any substance that is not present naturally in the lignocellulosic biomass. It is more generally an organic or chemical element, or a substance contained in the biomass in an abnormal amount (i.e., non-natural). An excess of contaminants, pollutants, dirt, or impurities can possibly lead to bacterial contamination. The contaminants are biological (bacteria, fungi, and other microorganisms), chemical (heavy metals), physical, or radiological substances. If the contaminants are waste and undesirable emissions, the term "pollution" is more appropriate (environmental pollution). The nature and the content of the contaminants can be easily determined by way of physicochemical analyses.

According to an advantageous embodiment, the adjusted parameter comprises at least one of the following parameters: severity factor, steam cracking pressure, steam cracking temperature, steam cracking duration, cessation of steam cracking, steam/solid ratio (washing, stripping), filling rate of the steam cracking tank, speed of advance in the continuous steam cracking tank.

According to variants:

- the measuring step consists in taking a sample of the biomass entering the steam cracking tank, and in applying a physicochemical analysis to the sample in order to characterize and quantify the contaminants present;
- the measuring step consists in taking a sample of the waste gases or liquids in or at the outlet of the steam cracking tank, and in applying a physicochemical analysis to the sample in order to characterize and quantify the contaminants present;
- the measuring step consists in taking a sample of a specimen of steam-cracked products in or at the outlet of the steam cracking tank, and in applying a physicochemical analysis to the sample in order to characterize and quantify the contaminants present; and
- the measuring step consists in taking a sample of a specimen of pellets and in applying a physicochemical analysis to the sample in order to characterize and quantify the contaminants present.

According to a particular embodiment, at least some of the measurement results, as well as the results of the measurement performed on a specimen of pellets obtained during the same cycle, are recorded periodically, and time stamped.

According to another advantageous variant, the results are injected into a blockchain.

Advantageously, the injection is performed into a supervised learning system in order to produce the digital model.

According to a variant, the model is determined by a series of chemical simulations. The present disclosure also relates to a facility for implementing this method.

BRIEF DESCRIPTION OF THE DRAWINGS

The present disclosure will be more clearly understood upon reading the following detailed description, which refers to the accompanying drawings and relates to a non-limiting embodiment of the present disclosure, in which drawings:

FIG. 1 is a schematic view of a facility for discontinuous steam cracking, but the general principle applies for a continuous method.

DETAILED DESCRIPTION

Steam Cracking of Contaminated Biomass

In addition to the known effect of steam cracking for reducing the fibers into powder and homogenizing the biomasses, the effect of the steam treatment would make it possible to extract the extractable compounds made volatile by the partition of the minor or major molecules or elements in the vapor phase, or by chemical depolymerization reactions. Thus, heavy metals such as zinc can volatilize, plastics materials would be hydrolyzed and vaporized, chlorinated or nitrogenated compounds would be extracted, biological compounds would be inactivated.

The method according to the present disclosure does not clean the biomass but modifies the concentrations in the solid fraction and enriches the gas fraction. The treatment of a volatile substance by conventional systems for treatment of waste gases, by washing, complexation or by combustion, is easier than on a solid fraction. Furthermore, the solid residue would see the reduction in concentration of some components—halogenated compounds, heavy metals, major elements (nitrogen, chlorine). These are elements widely pursued for the use of steam-cracked biomass in combustion (in the form of black pellets). However, the nature of the volatiles, their cleanup by combustion, and their possible toxicity, must be apprehended by rigorous analyses.

By acting on the treatment conditions (duration, temperature and thus severity), and by following the volatile emissions of compounds (chlorine, for example, but also heavy metals), as well as the tracers of fossil plastics polymers or of chemical treatment on the solid fraction, it is possible to orientate the partition of the molecules and to obtain a black pellet that contains fewer additives, allowing for uses that would have generally been limited.

Description of an Embodiment of a Facility

FIG. 1 is a schematic view of a facility for steam cracking or explosion of biomass. The facility for steam explosion includes an evaporator (100) that generates steam, and a reactor (200) that is subjected to rapid decompression.

The facility comprises a steam cracking reactor (200) and a spark arrestor (300). The reactor (200) is filled with biomass via the valve (13). Following closure of the valve (13), the steam is introduced into the reactor via the charging valve (6). The reactor (200) is then allowed to reach the target temperature, before starting the time period at the desired temperature. Typically, approximately 20 seconds are required for reaching the desired temperature. At the end of the desired period, the valve (9) is opened to allow the explosive decompression. The steam-exploded material passes through the connection pipe and fills the spark arrestor (300).

A high-pressure pump (1) supplies the steam generator (100). Heating bands (2) ensure the thermostabilization of the various items of equipment.

The facility furthermore comprises pressure gauges and sensors (3) for measuring the pressure and the temperature in the steam generator (100), as well as a pressure gauge and sensor (4) for measuring the pressure and the temperature in the reactor (200). An isolating valve (5) controls the entry of the steam into the generator (100). A safety valve (7) limits the pressure in the steam generator (100). The reactor (200) also comprises a safety valve. The spark arrestor (300) is equipped with a pressure gauge (12). The supply of the reactor (200) is achieved by a supply chamber (14), which draws along a controlled volume of the biomass stored in a reserve (15).

The facility comprises one or more items of sampling equipment (50 to 54) for solid, liquid or gaseous specimens, for analyzing the content of contaminants. These data are processed by a programmable machine (16) that controls the parameters of the facility, depending on the result of the analyses and the parameters provided by the pressure and temperature sensors. The data are furthermore stored in a memory (17), which also contains the recording of the processing model determining the parameters to apply, depending on the result of the analyses.

This memory (17) is associated with a computer that applies supervised learning processing to the historical data stored in the memory (17), and that also controls the injection of the data into a blockchain.

Severity factor and control of the facility.

The control measures for the treatment of a contaminated biomass takes into account the optimal elimination conditions, in the reactor (200), of some of the contaminants.

The control measures of the parameters and of the operating point are thus selected not merely depending on the processes of destructuration of the lignocellulosic materials, but also on their effect on the evaporation or the destruction of some contaminants or the decontamination reactions.

For this purpose, a digital model of control measures is developed, suitable for each contaminant and for each contaminant combination, in order to have available a digital reference that makes it possible to automatically adapt the parameters, depending on the nature of the biomass entering the reactor (200).

The construction of this model can be carried out experimentally, performing a succession of treatments of various contaminated biomasses, having different control measures, in order to retain the control measures corresponding to the minimization of the contaminants still present in the pellets produced.

This model can also be drawn up by a supervised learning solution, from recorded historic data.

Finally, the model can be drawn up by simulation of chemical reactions relating to the main contaminants that may be present in some biomasses.

This model determines the control measures to be selected, for each class of contaminants.

During a new treatment, the physicochemical analyses provide the nature and the composition of the contaminants, and a computer automatically determines the control measures of the facility, depending on the result of the analyses, and on the recorded digital model.

The pellets thus produced all have the same calorific qualities, furthermore improving the sterility and biological safety of the pellets, despite being obtained from contaminated biomass, in particular, biological contaminants (fungi, bacteria, etc.).

The invention claimed is:

1. A method for producing a solid biofuel by continuous or discontinuous steam cracking of lignocellulosic biomass, the method comprising:

introducing a biomass comprising a contaminated lignocellulosic biomass into a steam cracking reactor, the contaminated lignocellulosic biomass comprising at least one contaminant;

taking a sample of specimen in or at an outlet of the steam cracking reactor at least once during the steam cracking process;

physicochemical analyzing the sample of specimen to identify a chemical nature and to determine an amount of the at least one contaminant contained in the sample of specimen; and adjusting at least one parameter of the steam cracking process based on analysis results of the at least one contaminant contained in the sample of specimen and on a digital model of optimal steam cracking parameters corresponding to the chemical nature and the amount of the at least one contaminant.

2. The method of claim 1, wherein the at least one parameter is selected from among the following group of parameters: severity factor, steam cracking pressure, steam cracking temperature, steam cracking duration, cessation of steam cracking, steam/solid ratio, filling rate of a steam cracking tank, speed of advance in a steam cracking tank, rate of compression at an inlet, rate of compression at an outlet of a discharge of the reactor with an orifice diameter, supply flow rate, humidity, or particle size.

3. The method of claim 1, wherein the contaminated lignocellulosic biomass has a humidity of less than 27% at time of introducing the contaminated lignocellulosic biomass into the steam cracking reactor.

4. The method of claim 1, wherein taking the sample of specimen in or at the outlet of the steam cracking reactor at least once during the steam cracking process comprises taking a sample of solid specimen, liquid specimen, or gaseous specimen in or at the outlet of the steam cracking reactor.

5. The method of claim 1, further comprising:

taking a sample of pellet specimen produced from the steam cracking process; and physicochemical analyzing the sample of pellet specimen to determine the chemical nature and content of the at least one contaminant contained therein.

6. The method of claim 1, wherein the digital model is determined by a series of chemical simulations.

7. The method of claim 1, further comprising periodically recording and time stamping at least some results of the chemical nature and the amount of the at least one analyzed contaminant.

8. The method of claim 7, further comprising injecting the at least some results into a blockchain.

9. The method of claim 7, further comprising injecting the at least some results into a supervised learning system for producing the digital model.

* * * * *